United States Patent [19]

Beckmann et al.

[11] Patent Number: 4,538,125
[45] Date of Patent: Aug. 27, 1985

[54] DEVICE FOR MICROWAVE TRANSMISSION BETWEEN TWO BODIES WHICH ARE ROTATABLE RELATIVE TO EACH OTHER

[75] Inventors: Friedrich K. Beckmann, Schenefeld; Wolfgang Hoppe, Norderstedt; Wolfgang Meyer, Henstedt-Ulzburg, all of Fed. Rep. of Germany

[73] Assignee: U.S. Philips Corporation, New York, N.Y.

[21] Appl. No.: 487,406

[22] Filed: Apr. 21, 1983

[30] Foreign Application Priority Data

Apr. 24, 1982 [DE] Fed. Rep. of Germany ....... 3215377

[51] Int. Cl.³ ............................................... H01P 1/00
[52] U.S. Cl. .................................... 333/248; 333/256; 343/763
[58] Field of Search ................ 343/763, 767, 769–772, 343/776, 783; 333/248, 256, 261

[56] References Cited

U.S. PATENT DOCUMENTS

| | | | |
|---|---|---|---|
| 2,737,633 | 3/1956 | Tomiyasu | 333/256 |
| 3,189,855 | 6/1965 | Forrer | 333/256 |
| 3,419,826 | 12/1968 | MacWilliams et al. | 333/248 |
| 4,358,746 | 11/1982 | Miller et al. | 343/763 |

Primary Examiner—Eli Lieberman
Assistant Examiner—Michael C. Wimer
Attorney, Agent, or Firm—Marc D. Schechter

[57] ABSTRACT

The invention relates to a device for transmitting microwaves between two bodies which are rotatable relative to each other. Two annular waveguides are arranged on a common axis. Each waveguide has a coupling slot along its circumference. A transmitting aerial projects into each coupling slot and is moveable relative to the associated waveguide. The electromagnetic waves generated by the transmitting aerials are received by receiving aerials at the ends of the waveguides, respectively. The outputs of the receiving aerials are prepared for further processing.

6 Claims, 4 Drawing Figures

DEVICE FOR MICROWAVE TRANSMISSION BETWEEN TWO BODIES WHICH ARE ROTATABLE RELATIVE TO EACH OTHER

BACKGROUND OF THE INVENTION

The invention relates to devices for microwave transmission between two bodies which are rotatable relative to each other. Such devices are sometimes known as microwave slip rings. Such a device has two circular waveguides arranged on an axis. Each waveguide comprises a receiving and a transmitting aerial and has along its circumference a coupling slot. Two of the four aerials project into the two coupling slots and are movable therein. These two aerials are mechanically coupled together. The two other aerials are fixed to the associated waveguides.

Such a device is disclosed in U.S. Pat. No. 3,419,826. As described in that patent, the device can be used for telephone connections for rotating apartment houses, for a radar aerial, or for an airfield control tower.

Contactless transmission of information is also needed in computer tomography devices. In these devices, X-rays are passed through a patient and are detected by a plurality of X-ray detectors. The detectors and the X-ray source are fitted on a member which rotates around the patient. The detector signals from the rotating member must then be transmitted to a stationary member so that they can be processed by a computer. When the radiator rotates more than once around the patient, transmission of the detector signals via cables is no longer possible. The information can then be transmitted by the device described above when the transmission rate or the data stream is sufficiently large.

In the prior art arrangement, one waveguide is semicircular and is closed at both ends by attenuators. The other waveguide is a closed ring. An attenuator is provided in the closed ring to prevent a wave from circulating more than once in the ring. A changeover switch is provided which, depending on the positions of the receiving aerials projecting into the coupling slot, renders either the one or the other receiving aerial operative.

In certain circumstances in the prior art device, an electromagnetic wave must travel substantially completely around the waveguide ring before it arrives at the receiving aerial. In the semicircular waveguide, the maximum wave path is only half as long. As a result, sudden changes are produced in the propagation time when the receiving aerials are changed over. These sudden changes considerably impede continuous signal transmission at a high transmission rate.

The sudden changes in the propagation time do not occur in the embodiment shown in FIG. 6 of U.S. Pat. No. 3,419,826. However, this embodiment requires two changeover switches which alternately connect one out of two transmitting aerials to one out of two receiver aerials. The changeover switches must always be changed over at the correct moment, which requires complicated and expensive electronic circuitry.

SUMMARY OF THE INVENTION

It is an object of the invention to provide a device for transmitting microwave between a stationary body and a rotating body of such a construction that a changeover between the transmitting and the receiving aerials, respectively, is not required.

According to the invention this is accomplished in that:

(a) each waveguide is closed by the aerial which is fixed to it, (b) a sector of each waveguide is separated from this aerial by an attenuator, so that the remaining portion of the waveguide between this aerial and the attenuator is approximately half a circular arc, and (c) the two waveguides are arranged such that (1) at least one of the two movable aerials projects into that portion of the coupling slot of a waveguide which is located between the attenuator and the aerial which is in a fixed position relative to the waveguide, and (2) the direction of rotation of the electromagnetic waves from the transmitting aerials to the associated receiving aerials are opposite to each other in the two waveguides.

The fixed aerial which terminates each waveguide and the attenuator divide each waveguide into an active sector and a passive sector. When the aerial which is movable relative to the waveguide moves into the active sector in the coupling slot, signals are transmitted between the transmitting and receiving aerials. If, in contrast, the aerial moves into the passive sector, transmission between the two aerials becomes substantially impossible. The active and the passive sectors of the two waveguides are arranged such that at least one aerial is always in the active region of the waveguide.

When the aerials which project into the coupling slots are moved along the circumferences of the waveguide, the propagation time of the electromagnetic waves between the receiving and the transmitting aerials of a waveguide first increases. The propagation time increases until the aerial which projects into the coupling slot has reached the region in which the attenuator is fitted. At that moment, the other aerial which projects into the coupling slot moves into the active sector such that the propagation time in the two waveguides is the same.

When rotation continues, the other aerial projecting into the coupling slot transmits microwaves (while the first-mentioned aerial moves through the passive sector and is rendered inoperative there). The propagation time then decreases to a minimum. At this time, the first-mentioned aerial again moves into the active sector while the other aerial moves into the passive sector. As a result, with continuous rotation the propagation time does not change suddenly. The propagation time changes gradually so that high transmission rates are possible in practice.

DESCRIPTION OF THE PREFERRED EMBODIMENTS

Figure 1:
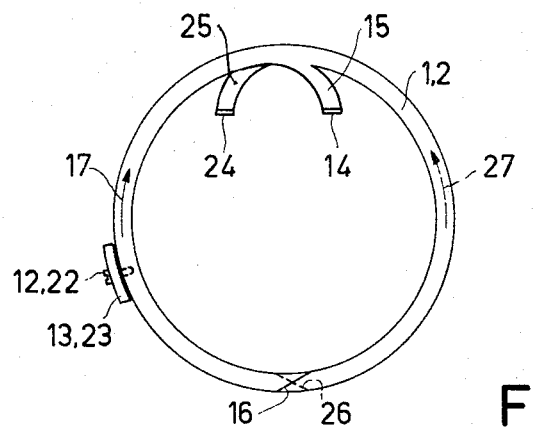
FIG. 1 is a plan view of the waveguide arrangement according to the invention.
Figure 2:
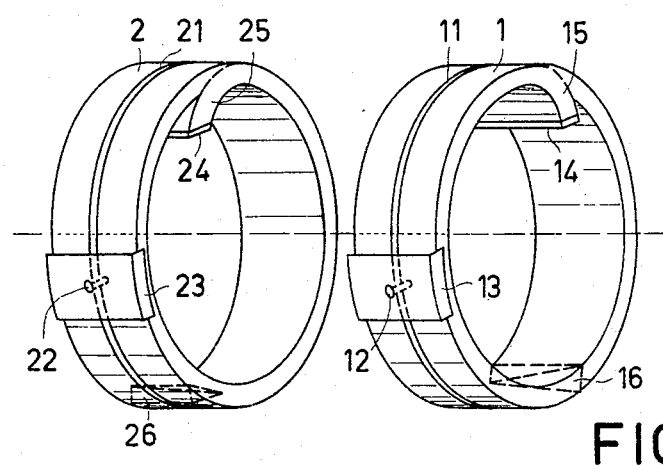
FIG. 2 is a perspective, expanded view of the waveguide arrangement (not to scale).

FIG. 1 and more specifically FIG. 2 show two annular waveguides 1 and 2 of rectangular cross-sections. In the center of the exterior surfaces of each waveguide, there is a coupling slot 11 and 21, respectively. Transmitting aerials 12 and 22 project into slots 11 and 21, respectively. The transmitting aerials 12 and 22 are fitted to slides 13 and 23, respectively. Slides 13 and 23 are movably arranged on the associated waveguides 1 and 2, respectively.

For transmitting signals between a rotating and a non-rotating member (both members are not shown in the drawing) the waveguides 1 and 2 on the one hand and the slides 13 and 23 on the other hand are each coupled to these two members. Hereinafter it will be assumed that the slides 13 and 23 are connected to the rotatable member and the waveguides 1 and 2 are coupled to the fixed member. However, it would not make any difference if it were the other way round.

When rotated, the slides 13 and 23 move on the waveguides 1 and 2, respectively. Consequently the aerials 12 and 22 move in the coupling slots 11 and 21, respectively.

Although the two waveguides 1 and 2 are of a circular shape an electromagnetic wave cannot circulate therein more than once, as they are each closed at their ends by receiving aerials 14 and 24, respectively. Aerials 14 and 24 are only shown schematically in the drawing. The aerials are arranged such that the receiving aerial 14 receives only electromagnetic waves which rotate clockwise. The receiving aerial 24 only receives electromagnetic waves which rotate counterclockwise. For this purpose the two waveguide ends 15 and 25 which support the receiving aerials are curved in the opposite direction into the interior of the circle. Alternatively, it is possible to terminate the waveguide in a reflection-free manner in a certain place. It is then necessary to arrange the two receiving aerials on different sides of these reflection-free terminations.

Arranged in the waveguides 1 and 2 are attenuators 16 and 26, respectively. The attenuators divide the waveguides into two segments which are electromagnetically decoupled from each other. The attenuators also terminate the waveguides and eliminate reflections of electromagnetic waves coming from the directions of the receiving aerials.

When the aerials 12 and 22 move into the portions of the coupling slots which are located between the attenuator and the receiving aerial (this sector being referred to as the "active" sector), signals are transmitted to the associated receiving aerials 14 and 24, respectively. If, in contrast, the transmitting aerials 12 and 22 move into the other sector (hereinafter referred to as the "passive" sector), signals cannot be so transmitted. For the waveguide 1 the active sector or region is located approximately in the left half of the waveguide ring. The passive sector is located approximately in the right half thereof. For waveguide 2, the active and passive sectors are oppositely located.

In the positions shown in the drawing, the transmitting aerial 12 is in the active sector, while the transmitting aerial 22 is in the passive sector. As a result, the energy radiated by aerial 22 cannot reach the associated receiving aerial 24. When the slides 13 and 23 are moved clockwise along the circumferences of the waveguide rings 1 and 2, respectively, the energy radiated by the transmitting aerial 12 (clockwise, in the direction of the arrow 17) continues to reach the receiving aerial 14. However, the propagation time of the electromagnetic wave becomes shorter. The propagation time continues to decrease until the slides 13 and 23 reach the regions of the ends 15 and 25, respectively, of the waveguides 1 and 2, respectively, so that the distances between the transmitting and receiving aerials is equal. Both transmitting aerials are now in the active sector. The propagation time has then reached its minimum.

When the slides 13 and 23 are rotated further in the clockwise direction beyond the described point, the transmitting aerial 12 enters the passive sector of the waveguide 1. The transmitting aerial 22 moves into the active sector of the waveguide 2, so that the electromagnetic waves propagate in the waveguide counterclockwise in the direction indicated by the arrow 27 (FIG. 1). The propagation time of the electromagnetic waves then continuously increases as the rotation continues.

The two attenuators 16 and 26 are arranged in the region located opposite to the ends 15 and 25, respectively, of the waveguides 1 and 2. As a result, the active sectors extend over at least half the circumferences of the waveguide arcs—but not further to any worthwhile extent. When the slides 12 and 22 reach the regions in which the attenuators 16 and 26, respectively, are provided, the transmitting aerial 12 moves from the passive sector to the active sector, and the aerial 22 moves from the active sector to the passive sector. The propagation times of the electromagnetic waves are the same and at their maximum in both waveguides.

When the slides 13 and 23 are then rotated still further in the clockwise direction, the situation shown in FIG. 1 is restored.

Figure 3:
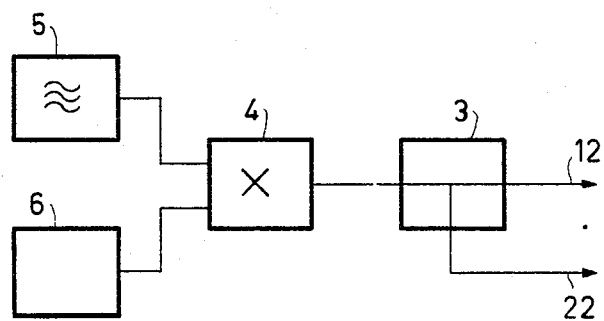
FIG. 3 is a block circuit diagram of a circuit for feeding the transmitting aerial of the waveguide arrangement.

As shown in FIG. 3, the transmitting aerials 12 and 22 are connected to a microwave power divider 3. The input of the power divider 3 is connected to an output of a microwave mixer 4. Mixer 4 mixes the signals from an oscillator 5 having a suitable carrier frequency, for example 10 GHz, with the signals from a data transmitter 6. The lowest frequency in the signal transmitted in the transmitter 6 is located above a predetermined cutoff frequency $f_g$.

Figure 4:
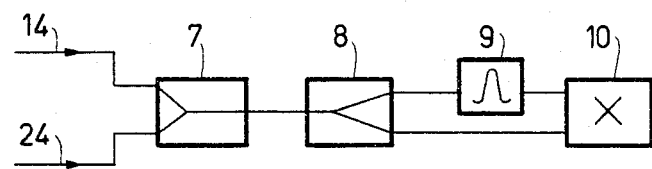
FIG. 4 is a block circuit diagram of a circuit for processing the signals from the receiving aerials of the waveguide arrangement.

As shown in FIG. 4, the signals which are received by the receiving aerials 14 and 24 are superimposed in a super-position stage 7. Connected to the output of the super-position stage 7 is a power divider 8. One output of divider 8 is directly connected to one input of a mixer stage 10. The other output of divider 8 is connected to a narrow band filter 9 whose output is connected to the other input of the mixer 10. The center frequency of the filter 9 corresponds to the carrier frequency. The bandwidth of filter 9 is less than twice the cutoff frequency, $f_g$, so that only the carrier frequency is present in the output signal from filter 9. This signal is mixed with the received signal in the mixer stage 10 so that at the output of the mixer stage 10 there is again a signal which corresponds to the signal produced by the data transmitter.

What is claimed is:

1. A microwave slip ring comprising:
   a first waveguide arranged at least partly around an axis, said first waveguide having first and second ends and a coupling slot therein extending around the axis between the first and second ends;
   a first fixed aerial arranged in the first waveguide at the first end thereof;
   a first attenuator in the first waveguide, said attenuator and the first end of the first waveguide defining an active sector therebetween, said active sector having an end at the aerial and an end at the attenuator, microwave energy propagated in the active sector of the first waveguide interacting with the first fixed aerial;

a first moveable aerial rotatable around the axis, said first moveable aerial projecting into the coupling slot and into the active sector of the first waveguide, said moveable aerial projecting into the active sector over an angular range approximately equal to 180°;

a second waveguide arranged at least partly around the axis and axially spaced from the first waveguide, said second waveguide having first and second ends and a coupling slot therein extending around the axis between the first and second ends;

a second fixed aerial arranged in the second waveguide at the first end thereof;

a second attenuator in the second waveguide, said second attenuator and the first end of the second waveguide defining an active sector therebetween, said active sector having an end at the aerial and an end at the attenuator, microwave energy propagated in the active sector of the second waveguide interacting with the second fixed aerial;

a second moveable aerial coupled to the first moveable aerial so as to be rotatable around the axis therewith, said second moveable aerial projecting into the coupling slot and into the active sector of the second waveguide, said second moveable aerial projecting into the active sector of the second waveguide over an angular range approximately equal to 180° ;

characterized in that the first and second waveguides and the first and second moveable aerials are arranged so that:

the first moveable aerial rotates out of the active sector of the first waveguide near the aerial end of the active sector of the first waveguide when the second moveable aerial rotates into the active sector of the second waveguide near the aerial end of the active sector of the second waveguide; and the second moveable aerial rotates out of the active sector of the second waveguide near the attenuator end of the active sector of the second waveguide when the first moveable aerial rotates into the active sector of the first waveguide near the attenuator end of the active sector of the first waveguide.

2. A microwave slip ring as claimed in claim 1, characterized in that when the first moveable aerial rotates out of the active sector of the first waveguide and the second moveable aerial rotates into the active sector of the second waveguide, the first moveable aerial is spaced from the first fixed aerial by a distance equal to a distance between the second moveable aerial and the second fixed aerial.

3. A microwave slip ring as claimed in claim 2, characterized in that when the first moveable aerial rotates into the active region of the first waveguide and the second moveable aerial rotates out of the active region of the second waveguide, the first moveable aerial is spaced from the first fixed aerial by a distance equal to a distance between the second moveable aerial and the second fixed aerial.

4. A microwave slip ring as claimed in claim 3, characterized in that the fixed aerials are receiving aerials and the moveable aerials are transmitting aerials.

5. A microwave slip ring as claimed in claim 4, characterized in that the slots do not extend all the way to the first ends of the waveguides.

6. A microwave slip ring as claimed in claim 5, characterized in that the fixed aerials close the ends of the associated waveguides.

* * * * *